(12) United States Patent
Kim

(10) Patent No.: US 10,471,119 B2
(45) Date of Patent: Nov. 12, 2019

(54) COMPOSITION FOR PREVENTING, AMELIORATING, OR TREATING NEUROLOGICAL DISEASE CONTAINING OSMOTIN PEPTIDE AS ACTIVE INGREDIENT

(71) Applicant: INDUSTRY-ACADEMIC COOPERATION FOUNDATION GYEONGSANG NATIONAL UNIVERSITY, Gyeongsangnam-do (KR)

(72) Inventor: Myeong Ok Kim, Gyeongsangnam-do (KR)

(73) Assignee: INDUSTRY-ACADEMIC COOPERATION FOUNDATION GYEONGSANG NATIONAL UNIVERSITY, Gyeongsangnam-Do (KR)

( * ) Notice: Subject to any disclaimer, the term of this patent is extended or adjusted under 35 U.S.C. 154(b) by 0 days.

(21) Appl. No.: 15/553,095

(22) PCT Filed: Mar. 3, 2016

(86) PCT No.: PCT/KR2016/002123
§ 371 (c)(1),
(2) Date: Aug. 23, 2017

(87) PCT Pub. No.: WO2016/140527
PCT Pub. Date: Sep. 9, 2016

(65) Prior Publication Data
US 2018/0036365 A1    Feb. 8, 2018

(30) Foreign Application Priority Data
Mar. 4, 2015    (KR) .................. 10-2015-0030455

(51) Int. Cl.
*A61K 38/08*    (2019.01)
(52) U.S. Cl.
CPC .................. *A61K 38/08* (2013.01)
(58) Field of Classification Search
None
See application file for complete search history.

(56) References Cited

U.S. PATENT DOCUMENTS

| 9,352,018 B2 * | 5/2016 | Kim | ................. A61K 38/168 |
| 2006/0069024 A1 | 3/2006 | Bressan et al. | |

| 2011/0318782 A1* | 12/2011 | Huang | ............... C07K 14/415 435/69.1 |
| 2013/0210738 A1* | 8/2013 | Kim | .................. A61K 38/168 514/17.6 |
| 2017/0246245 A1* | 8/2017 | Kim | .................. A61K 9/0019 |

FOREIGN PATENT DOCUMENTS

| KR | 10-1308232 B1 | 11/2013 | |
| KR | 10-1369701 B1 | 3/2014 | |
| KR | 10-1473966 B1 | 12/2014 | |
| WO | WO-2011090270 A2 * | 7/2011 | ........... A61K 38/168 |
| WO | WO-2015083871 A1 * | 6/2015 | ........... A61K 38/168 |

OTHER PUBLICATIONS

Sano, Curr Neurol Neurosc Rep 2: 392-399, 2002; abstract.*
Steece-Collier et al., PNAS USA 99(22): 13972-13974, 2002.*
Feigin et al., Curr Opin Neurol 15: 483-489, 2002.*
Yoon et al, Soc Neurosc abstract, poster presented on Nov. 13, 2013.*
Singh et al (Plant Physiol 90: 1096-1101, 1989).*
Chan et al (PLOS ONE 7: 1-12. 2012).*
International Search Report for PCT/KR2016/002123, dated Jul. 8, 2016.
NCBI, GenBank accession No. CAH69228.1, Nov. 3, 2004.
Marco Miele et al., "Structural and Functional Similarities between Osmotin from Nicotiana Tabacum Seeds and Human Adiponectin", PLoS ONE, vol. 6, Issue 2, Feb. 2011, pp. 1-11.
Jean-Francois Emard et al., "Neurodegenerative Diseases and Risk Factors: A Literature Review", Soc. Sci. Med. vol. 40. No. 6, 1995, pp. 847-858.

* cited by examiner

*Primary Examiner* — Daniel E Kolker
*Assistant Examiner* — Aditi Dutt
(74) *Attorney, Agent, or Firm* — The PL Law Group, PLLC

(57) ABSTRACT

A method of preventing or treating neurological disease includes administering to a subject in need thereof, a composition comprising an osmotin peptide selected from the group consisting of (a) an osmotin peptide having the amino acid sequence of SEQ ID NO: 1, and (b) an osmotin peptide having at least one amino acid residue substitution, deletion or insertion in the amino acid sequence of SEQ ID NO: 1. When a subject is treated with the osmotin peptide, nerve cells show no increase in growth rate, have little cytotoxicity, and suppress cell death, and when the osmotin peptide is administered to an animal model, the osmotin peptide infiltrated into the hippocampus of the brain and the hypothalamus of the brain, which is the deep part of the brain. Accordingly, the osmotin peptide is used as a composition for preventing, ameliorating, or treating neurological disease.

9 Claims, 14 Drawing Sheets
Specification includes a Sequence Listing.

COMPOSITION FOR PREVENTING, AMELIORATING, OR TREATING NEUROLOGICAL DISEASE CONTAINING OSMOTIN PEPTIDE AS ACTIVE INGREDIENT

CROSS REFERENCE TO RELATED APPLICATIONS AND CLAIM OF PRIORITY

This application claims benefit under 35 U.S.C. 119(e), 120, 121, or 365(c), and is a National Stage entry from International Application No. PCT/KR2016/002123, filed on Mar. 3, 2016, which claims priority to the benefit of Korean Patent Application No. 10-2015-0030455 filed in the Korean Intellectual Property Office on Mar. 4, 2015, the entire contents of which are incorporated herein by reference.

TECHNICAL FIELD

The present disclosure relates to a composition for preventing, ameliorating, or treating a neurological disorder containing osmotin peptide as an active ingredient.

BACKGROUND ART

Degenerative neurological disease means a gradual structural and functional loss of neurons. Degenerative neurological diseases develop mainly due to infiltration into particular sites of the nervous system, and can be accompanied by symptoms such as dementia, extrapyramidal abnormality, cerebellar abnormality, sensory disturbance, and movement disorders. In several cases, degenerative neurological diseases may develop due to simultaneous infiltration into various sites of the nervous system, and thus accompanied by complex symptoms. The diagnosis is made according to the clinical manifestation of the patient. In this case, it is difficult to accurately diagnose disease because the symptoms are various and different diseases have common clinical symptoms (Soc. Sci. Med. Vol. 40. No. 6, pp. 847-858, 1995).

Dementia, one of the neurological disorders, is a disorder accompanied by general impairment of systemic functions such as memory impairment and loss of judgment. Although the symptoms are rarely seen before age 50, their development frequency gradually increases after age 60. As the elderly population increases due to the development of medical technology and quality of life, the population having dementia is a rapidly growing worldwide as well as in Korea. The number of dementia patients aged 65 years or older registered in 2008 is 421,000, accounting for 8.4% of the total population of the elderly, and by 2030, the number is expected to be 1,135,000, or 9.6% of the total elderly population. In 2008, the Ministry of Health and Welfare studied the prevalence of dementia and found that dementia has various onsets. About 70% of domestic dementias are of Alzheimer type, about 25% of them are of vascular type, and the remaining 5% or less are other alcoholic dementia and Parkinson's disease dementia.

Alzheimer's disease (AD), the most onset type of dementia, has two distinct lesions: formation of neurofibrillary tangles inside cells by hyperphosphorylation and coagulation of tau proteins in the neurons of the cerebral cortex and hippocampus of the brain; and formation of a plague outside cells by the coagulation of amyloid β-1/42.

The cause of Alzheimer's disease has not yet been clearly identified, but it is said that the tangle or the plague, which is the coagulated form of two proteins involved in coagulation, or precursors are deposited on neural cell sites responsible for brain memory and recognition, leading to dysfunction and death of neurons, thereby causing Alzheimer's disease. Tau proteins are charged in stabilizing with microtubules. However, due to the coagulation, tau proteins are decreased in number and fail to perform their normal functions, resulting in weaker binding force with microtubules and a long-term dysfunction. Therefore, individual neurons deteriorate in terms of function and further die.

On the other hand, osmotin derived from plants is involved in fatty acid oxidation regulation, glucose uptake, phosphorylation (AMP kinase) and signal transduction pathways. Osmotin (24 kDa) is a stable protein belonging to the PR-5 family, which is homologous to the sweet-testing protein thaumatin, and is known to induce intracellular signaling in yeast. Osmotin is resistant to heat, acid, and enzymes and can circulate through the body without digestion. These osmotins are known to be homologues of adiponectin present in animals. Adiponectin has been known to have anti-inflammatory, anti-diabetic and anti-atherosclerotic potentials. Osmotin is widely known for its effects on obesity and diabetes, and Korean Patent No. 1308232 discloses a composition for the prevention and treatment of neurological disease, the composition containing osmotin. However, there are no known compositions including osmotin peptide alone to prevent or ameliorate, or treat neurological diseases.

SUMMARY

The present disclosure has been made in response to the above-mentioned needs, and is completed by confirming that an osmotin peptide including an amino acid sequence of SEQ ID NO: 1 increases the viability of neuronal cells, has little cytotoxicity, suppresses cell death, and when administered to an animal model, infiltrated into the hippocampus, the cerebral cortex, and even the hypothalamus, which is the deep part of the brain.

An aspect of the present disclosure provides a health functional food composition for preventing or ameliorating neurological disease, the health functional food composition including, as an active ingredient, osmotin peptide selected from: (a) an osmotin peptide having an amino acid sequence of SEQ ID NO: 1; and (b) an osmotin peptide having at least one amino acid residue substitution, deletion, or insertion in the amino acid sequence of SEQ ID NO: 1 and derived from (a) capable of preventing or ameliorating neurological disease.

Another aspect of the present disclosure provides a pharmaceutical composition for preventing or treating neurological diseases, the pharmaceutical composition including, as an active ingredient, osmotin peptide selected from (a) an osmotin peptide having an amino acid sequence of SEQ ID NO: 1; and (b) an osmotin peptide having at least one amino acid residue substitution, deletion, or insertion in the amino acid sequence of SEQ ID NO: 1 and derived from (a) capable of preventing or treating neurological disease.

Another aspect of the present disclosure provides a method of preventing or treating neurological disease including administering to an animal a composition including an osmotin peptide selected from: (a) an osmotin peptide having an amino acid sequence of SEQ ID NO: 1; and (b) an osmotin peptide having at least one amino acid residue substitution, deletion or insertion in the amino acid sequence of SEQ ID NO: 1 and derived from (a) capable of preventing or treating neurological disease.

When a composition containing an osmotin peptide according to the present disclosure is used, nerve cells can be protected from external stimuli or toxicity which inhibits their normal generation, development and growth. Accordingly, the composition can be useful for preventing, improving or treating neurological diseases. In addition, since the osmotin peptide according to the present disclosure consists of 9 amino acid sequences, its productivity through protein synthesis is high and thus industrial availability is high.

DETAILED DESCRIPTION

Figure 1A:
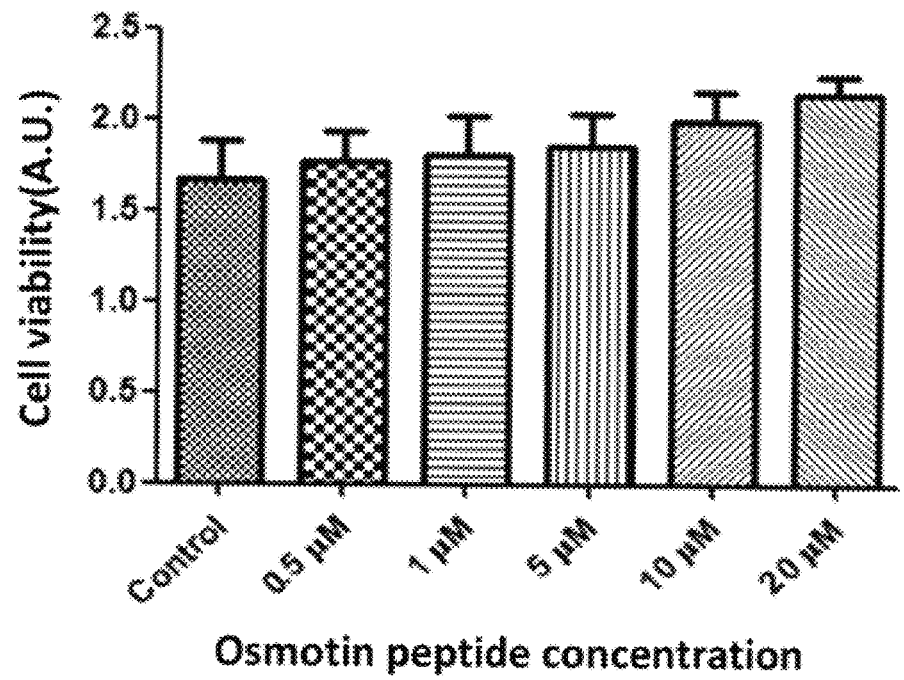
FIGS. 1A and 1B show the cell viability after 24 hours of treatment with osmotin peptide at a concentration from 0.5 to 20 μM in the human neuroblast line SH-SY5Y and hippocampal cell line HT22.

An aspect of the present disclosure provides a health functional food composition for preventing or ameliorating neurological disease, the health functional food composition including, as an active ingredient, osmotin peptide selected from: (a) an osmotin peptide having an amino acid sequence of SEQ ID NO: 1; and (b) an osmotin peptide having at least one amino acid residue substitution, deletion, or insertion in the amino acid sequence of SEQ ID NO: 1 and derived from (a) capable of preventing or ameliorating neurological disease.

According to the present disclosure, osmotin refers to a protein contained in a large amount in aged fruits such as grapes, and a protein consisting of about 150 to 250 amino acids depending on individuals. The osmotin peptide consisting of the amino acid sequence of SEQ ID NO: 1 is a peptide (SEQ ID NO: 1) consisting of 9 amino acids from 157th to 165th in the sequence of osmotin protein.

An osmotin peptide according to the present disclosure may be a purified natural product or a chemically synthesized product or may be obtained from recombinant techniques from prokaryotic or eukaryotic host cells (for example, bacteria, yeast, higher plant, insect, and mammalian cells).

According to the present disclosure, osmotin peptide refers to a peptide in which no more than 5, for example, no more than 3 amino acids have been replaced with amino acids with associated or similar properties compared to the amino acid sequence of SEQ ID NO: 1.

The neurological disorder may be one or more diseases selected from Alzheimer's disease, dementia, Parkinson's disease, epilepsy, schizophrenia, depression, bipolar disorder, neurogenic disorders, autism, stroke, Lou Gehrig's disease, Huntington's disease, and multiple sclerosis, but is not limited thereto. For example, the neurological disorder may be Alzheimer's disease. The osmotin peptide may be contained in an amount of 0.1 to 100% by weight based on the total weight of the health functional food composition.

The health functional food composition reduces the expression levels of Aβ oligomers, p-Tau (Ser413), and BACE-1 proteins in the hippocampus and cerebral cortex of the brain, increases the expression levels of SNAP25 and PSD95 proteins, and increases AdipoR1, pAMPK, total-AMPK, p-PI3K or pAkt (Ser473) proteins, and decreases the expression levels of pJNK or TNF-α protein.

The health functional food composition may be prepared in any form of food selected from a beverage, a pill, a tablet, a capsule, and powder, or may be added to other foods or ingredients of foods, by using a conventional method.

Examples of foods, to which the health functional food composition according to the present disclosure is added, include meat, sausage, bread, chocolate, candy, snack, confectionery, pizza, instant noodle, other noodles, gums, dairy products including ice cream, soups, beverage, tea, drinks, an alcoholic beverage, and a vitamin complex, and includes all the health foods in a conventional sense.

The health functional food composition may contain various nutrients, vitamins, minerals (electrolytes), synthetic and natural flavors, colorants and enhancers (cheese, chocolate etc.), pectic acid and salts thereof, alkynic acid and salts thereof, thickening agents, pH adjusting agents, stabilizers, preservatives, glycerin, alcohols, carbonating agents used in carbonated drinks, and the like. The health functional food composition may further contain fruit flesh for the production of natural fruit juices and vegetable drinks. These components may be used independently or in combination, and may additionally contain various flavors or natural carbohydrates. Examples of the natural carbohydrates include monosaccharides such as glucose and fructose; disaccharides such as maltose or sucrose; polysaccharides such as dextrin and cyclodextrin; and sugar alcohols, such as xylitol, sorbitol, and erythritol. Examples of the sweetening agent include natural sweetening agents such as Tau Martin and stevia extract, and synthetic sweetening agents such as saccharin and aspartame.

Another aspect of the present disclosure provides a pharmaceutical composition for preventing or treating neurological diseases, the pharmaceutical composition including, as an active ingredient, osmotin peptide selected from (a) an osmotin peptide having an amino acid sequence of SEQ ID NO: 1; and (b) an osmotin peptide having at least one amino acid residue substitution, deletion, or insertion in the amino acid sequence of SEQ ID NO: 1 and derived from (a) capable of preventing or treating neurological disease.

The pharmaceutical composition may further include, in addition to the active ingredient, at least one carrier selected from saline, sterilized water, a Ringers solution, buffered saline, dextrose solution, maltodextrin solution, glycerol, ethanol, lactose, dextrose, sucrose, sorbitol, mannitol, starch, acacia rubber, calcium phosphate, alginate, gelatin, calcium silicate, microcrystalline cellulose, polyvinylpyrrolidone, cellulose, syrup, methylcellulose, methylhydroxybenzoate, propylhydroxybenzoate, talc, magnesium stearate and minerals oil, each of which is pharmaceutically acceptable. The pharmaceutical composition may further contain, in addition to the active ingredient, at least one supplement selected from antioxidants, buffers, bacteriostats, diluents, surfactants, binders, lubricants, wetting agents, sweeteners, flavors, emulsifiers, suspending agents, and preservatives, each of which is pharmaceutically acceptable.

The pharmaceutical composition may be administered orally or parenterally in accordance with a conventional method. When the pharmaceutical composition is formulated, a conventionally used diluent or excipient, such as a filler, an extender, a binder, a wetting agent, a disintegrant, or a surfactant, may be used. Examples of solid formulations for oral administration include tablets, pills, powder, granules, capsules and the like, and such solid formulations may be prepared by using at least one excipient selected from starch, calcium carbonate, sucrose, lactose, gelatin and the like. In one embodiment, in addition to simple excipients, lubricants such as magnesium stearate and talc may be used. Examples of liquid preparations for oral administration include suspensions, solutions, emulsions, syrups and the like. Various excipients, such as wetting agents, sweeteners, fragrances, preservatives and the like, may be included in addition to water and liquid paraffin, which are commonly used, simple diluents. Examples of formulations for parenteral administration include sterile aqueous solutions, non-aqueous solutions, suspensions, emulsions, freeze-dried preparations, and suppositories. Examples of the non-aqueous solvent and the suspending agent include propylene glycol, polyethylene glycol, vegetable oil such as olive oil, injectable ester such as ethyl oleate, and the like. Examples of suppository bases include witepsol, macrogol, tween 61, cacao paper, laurin, glycerogelatin and the like.

Another aspect of the present disclosure provides a method of preventing or treating neurological disease, the method including administering to an animal a composition including an osmotin peptide selected from: (a) an osmotin peptide having an amino acid sequence of SEQ ID NO: 1; and (b) an osmotin peptide having at least one amino acid residue substitution, deletion or insertion in the amino acid sequence of SEQ ID NO: 1 and derived from (a) capable of preventing or treating neurological disease.

Hereinafter, the present disclosure will be described in more detail with reference to Examples. One of ordinary skilled in the art may understand that these examples are only for describing the present disclosure specifically and do not limit the scope of the present invention.

Example 1. Culture of Human Neuroblast Line SH-SY5Y Cells

Human neuroblast line SH-SY5Y cells were cultured in 100 µl of dulbecco modified eagle medium (DMEM) supplemented with 10% (v/v) fetal bovine serum (FBS) and 1% (w/v) antibiotic (penicillin-streptomycin) at 37° C. and under the condition of 5% $CO_2$.

Example 2. ApoTox-Glo™ Triplex Assay

Cells were seeded in a 96-well plate containing growth medium (DMEM medium containing 10% FBS, 100 units/ ml penicillin, and 100 mg/ml streptomycin) in such a way that 100 μl of the culture was seeded in every cell at the population of 2×10⁴ cells, and cultured under the condition of 5% $CO_2$ at 37° C. When cells were about 70-90% confluent, they were transformed with pCAX-APP Swe/Ind for 8 hours by using Lipofectamine 3000 according to the manufacturers instructions. Then, the medium was removed by suction and replaced with fresh 100 μl of growth medium containing 0.5 to 20 μM osmotin-peptide. The cells in the fresh medium were incubated for 24 hours.

After 24 hours, ApoTox-Glo™ Triplex assay using Glomax-Multi Detection system was performed according to the manufacturer's instructions to confirm cell viability, cytotoxicity assay, and caspase-3 activity.

Figure 1B:
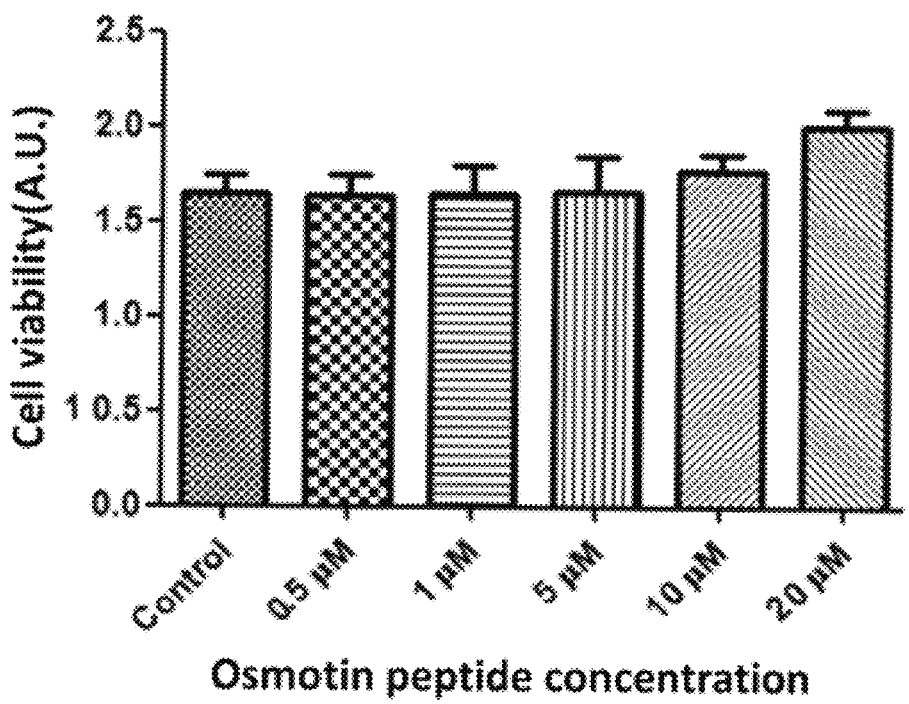

As a result, as shown in FIGS. 1A and 1B, it is seen that the cell viability was increased in proportion to the osmotin peptide treatment concentration.

Example 3 Morphological Analysis Using Immunofluorescence In Vitro

For morphological analysis, human neuroblast line SH-SY5Y cells were seeded at 2×10₄ cells/well in a 96-well plate and treated with osmotin peptide at concentrations of (1, 5 and 10 μg). The cells were cultured at a temperature of 37° C. under the condition of 5% $CO_2$ while a medium (DMEM medium containing 10% FBS, 100 Units/ml of penicillin and 100 mg/ml of streptomycin) was changed at regular intervals 7 times a day.

When the cells were 70 to 90% confluent, the medium was exchanged with fresh medium containing FITC-tagged osmotin-peptide (1, 5 and 10 μg) and further cultured for 24 hours. The cells were washed with PBS buffer and fixed with 4% (v/v) paraformaldehyde for 30 minutes at room temperature. After removing the 4% (v/v) paraformaldehyde, the cells were washed with PBS buffer for 5 minutes and infiltrated with 0.1% (v/v) Triton X-100 at room temperature for 15 minutes. Then, the cells were treated with a 1% BSA blocking solution at room temperature for 1 hour. After mounting the cover slip, sections were observed with a confocal microscope (Flouview FV1000).

Figure 2:
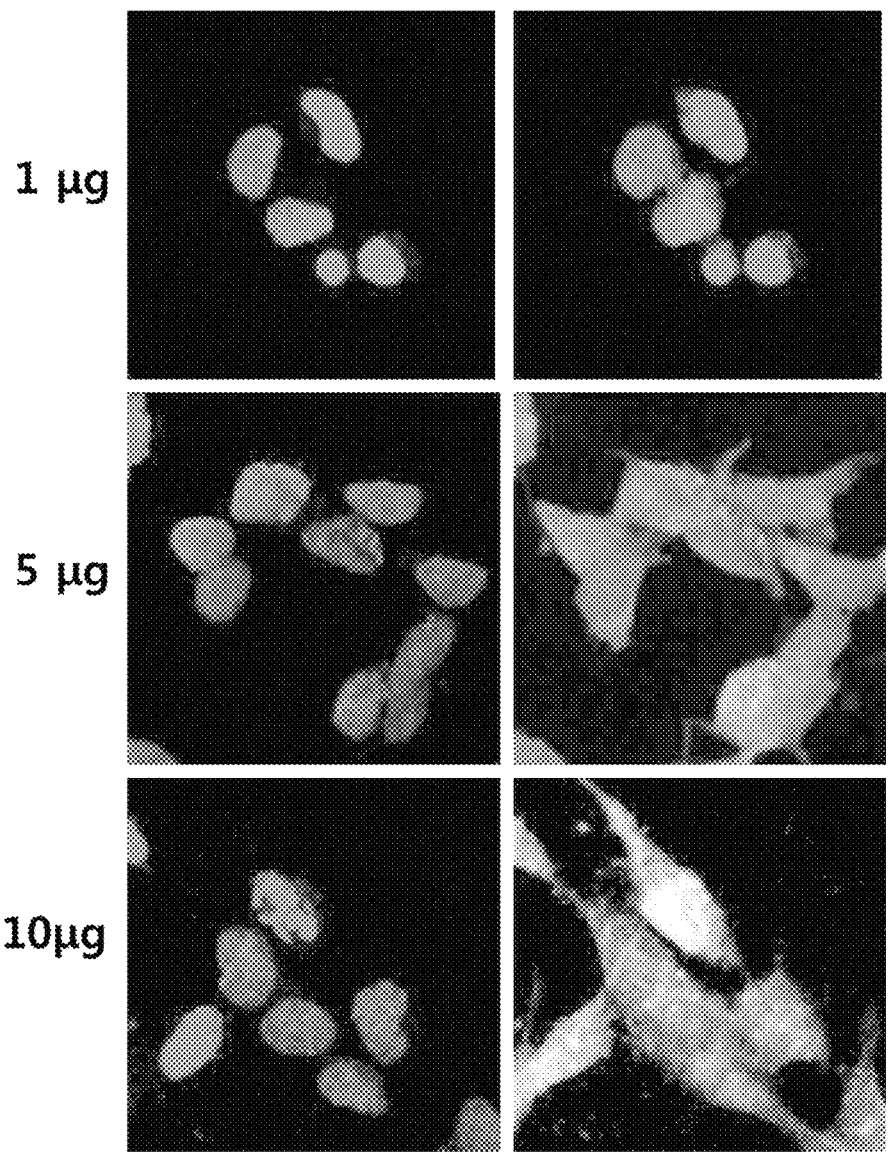
FIG. 2 shows fluorescence images of the human neuroblast line SH-SY5Y after the treatment with 1, 5 and 10 μg of osmotin peptide-FITC. Cobalt shows a neuroblast line SH-SY5Y, and green shows the human neuroblast line SH-SY5Y bound to osmotin peptide.

As shown in FIG. 2, it was confirmed that the osmotin peptide was bound to the cytoplasm of cells.

Example 4. Immunofluorescence Analysis of Brain after Intraperitoneal Injection and Tail Vein Injection of Osmotin Peptide Using Animal Model Ten weeks-old APP/PS1 mice were treated with osmotin-peptide by intraperitoneal (IP) injection once per day for 45 days, and then, slide sections thereof were prepared. Thioflavin-S staining for observing amyloid plaques was performed using cryosection washed in tap water for several minutes.

After incubation for 5 minutes in 0.25% potassium permanganate, the sections were incubated for 5 minutes in a solution containing 1% $K_2S_2O_5$ and 1% (v/v) oxalic acid, and were allowed to stand in 0.02% thioflavine-S solution for 8 minutes.

Subsequently, brain sections were washed twice with 80% (v/v) ethanol for 1 minute and then in slow running tap water for 4-5 minutes. Then, the brain sections were anhydrated by using (70, 80, and 95% (v/v)) xylene while the alcohol content was gradually increased. The sections were mounted with cover slips and observed with a confocal laser-scanning microscope (Flouview FV 1000).

In addition, osmotin peptide-FITC was administered to the mice by intraperitoneal (IP) injection and tail vein injection (IV). Four hours later, the mice were fixed by transcardial perfusion with 4% (v/v) ice-cold paraformaldehyde, and the brain was harvested and post-fixed in 4% (v/v) paraformaldehyde for 72 hours, and finally, transferred to a 20% (w/v) sucrose for 72 hours.

The brain was infiltrated with OCT (optimal cutting temperature compound) under liquid nitrogen, and a 14 μm coronal section was mounted on a ProbeOn Plus slide.

Slides for immunofluorescence analysis were washed twice with 0.01 M PBS buffer for 15 minutes. The sections were covered with proteinase K and incubated for 5 minutes in a humid chamber at the temperature of 37° C. Incubation was performed for one hour in a blocking solution containing 5% (v/v) normal goat serum dissolved in PBS buffer and 0.3% (v/v) Triton X-100. After the blocking process, the mounting cover slips and sections were observed on a confocal laser-scanning microscope (Flouview FV 1000).

Figure 3:
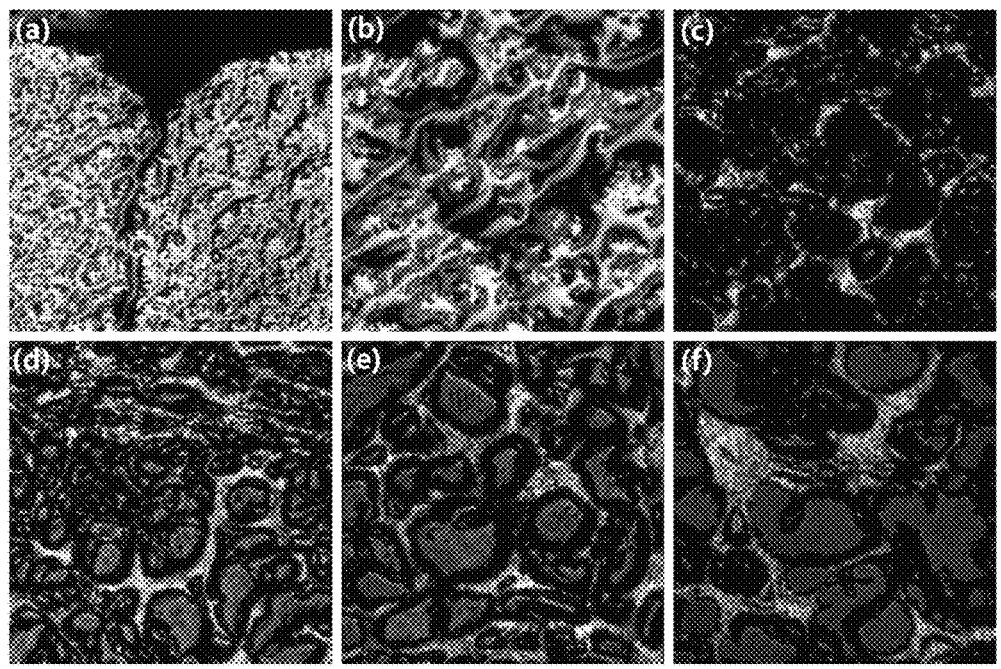
FIG. 3 shows fluorescent images for confirming that osmotin peptide-FITC, administered to mice by tail vein injection (IV) (a to c) and intraperitoneal (IP) injection (d to f), has transferred to the hippocampus site of the brain.
Figure 4:
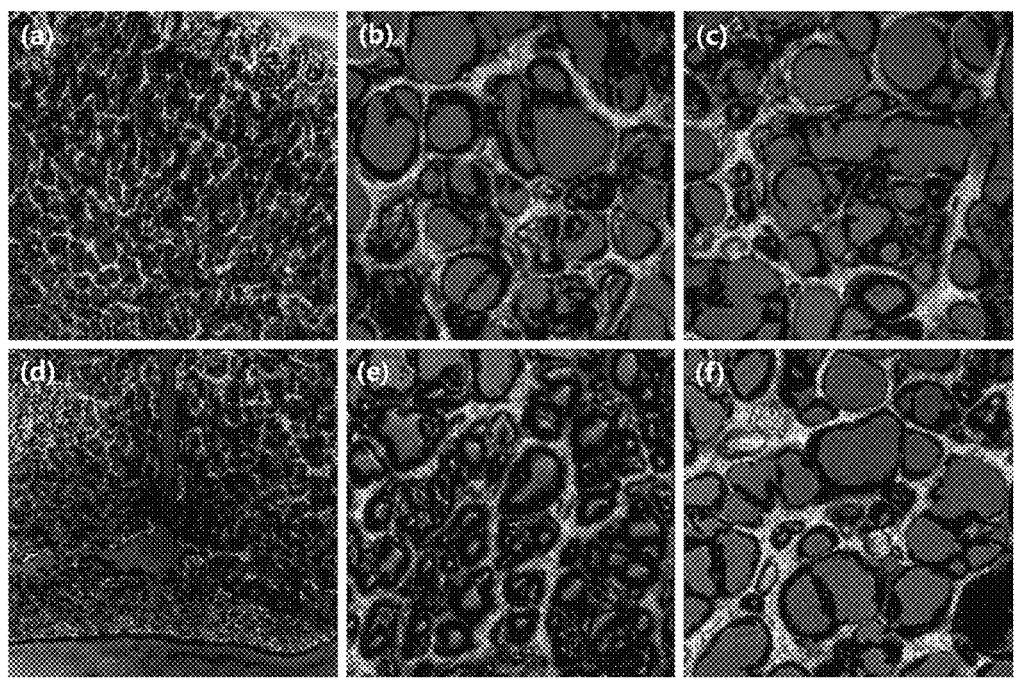
FIG. 4 shows fluorescence images for confirming that osmotin peptide-FITC administered to mice by intravenous injection has transferred to the cerebral cortex (a to c) and hypothalamus (d to t) of the brain. a is a low magnification view of the cerebral cortex, b and c are high magnification views of the cerebral cortex, d is a low magnification view of the hypothalamus, and e and f are high magnification views of the hypothalamus.
Figure 5A:
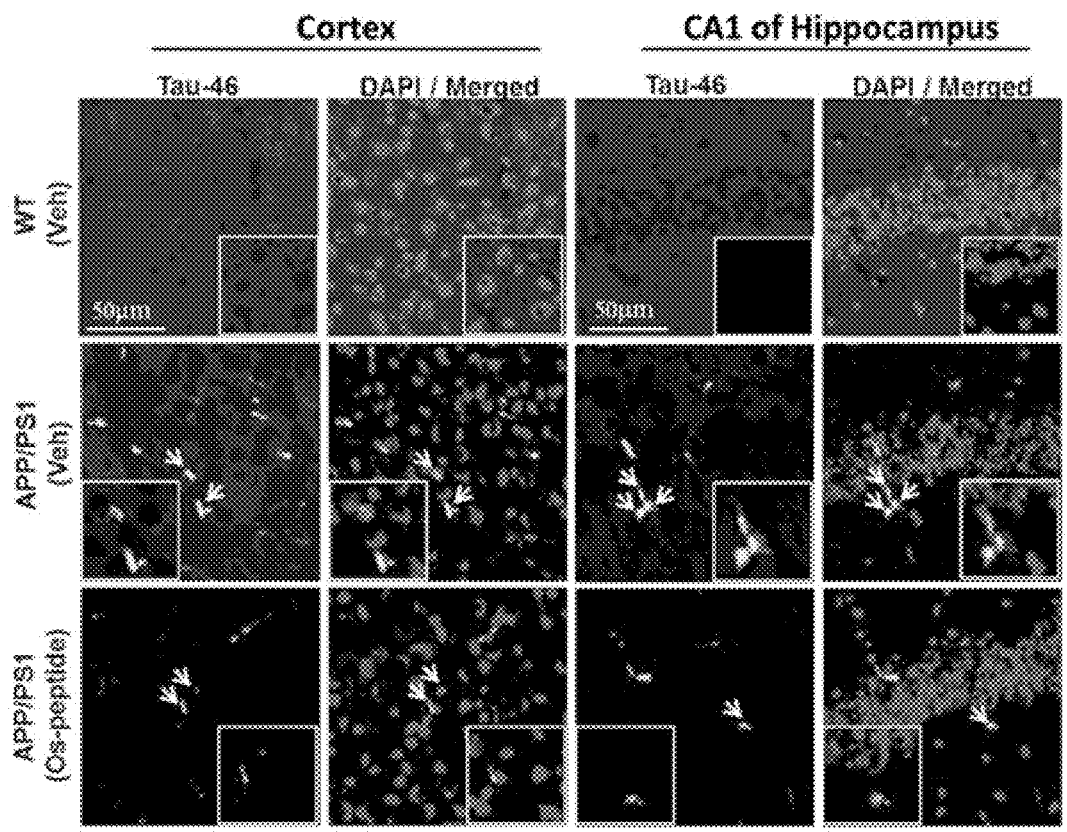
FIGS. 5A and 5B show that the expression of Tau-46 protein is decreased in the cerebral cortex and hippocampal sites when APP/PS1 mice are treated with osmotin peptide. *** indicates statistically significant increase in expression of Tau-46 in the APP/PS1 model compared to WT (normal control), and, in this case, the p value is less than 0.001. ### means that the expression of Tau-46 is statistically significantly reduced compared to the APP/PS1 model when osmotin peptide is treated, and, in this case, the p value is less than 0.001.
Figure 5B:
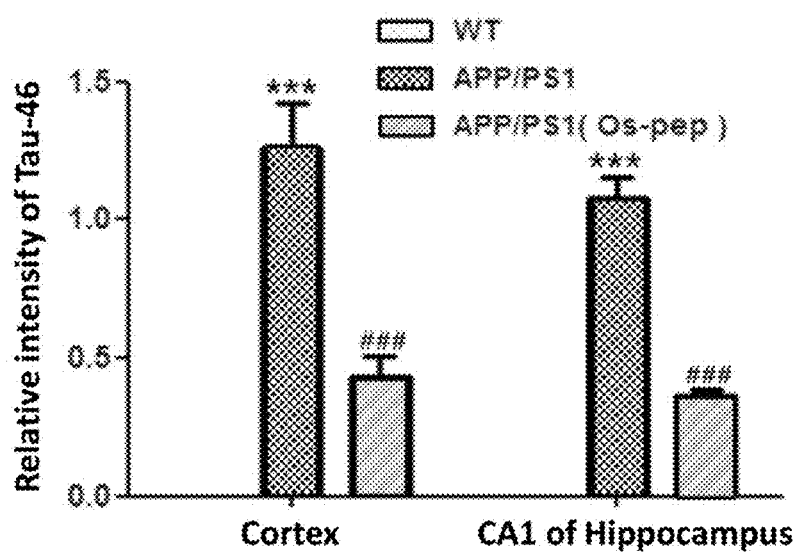
Figure 6A:
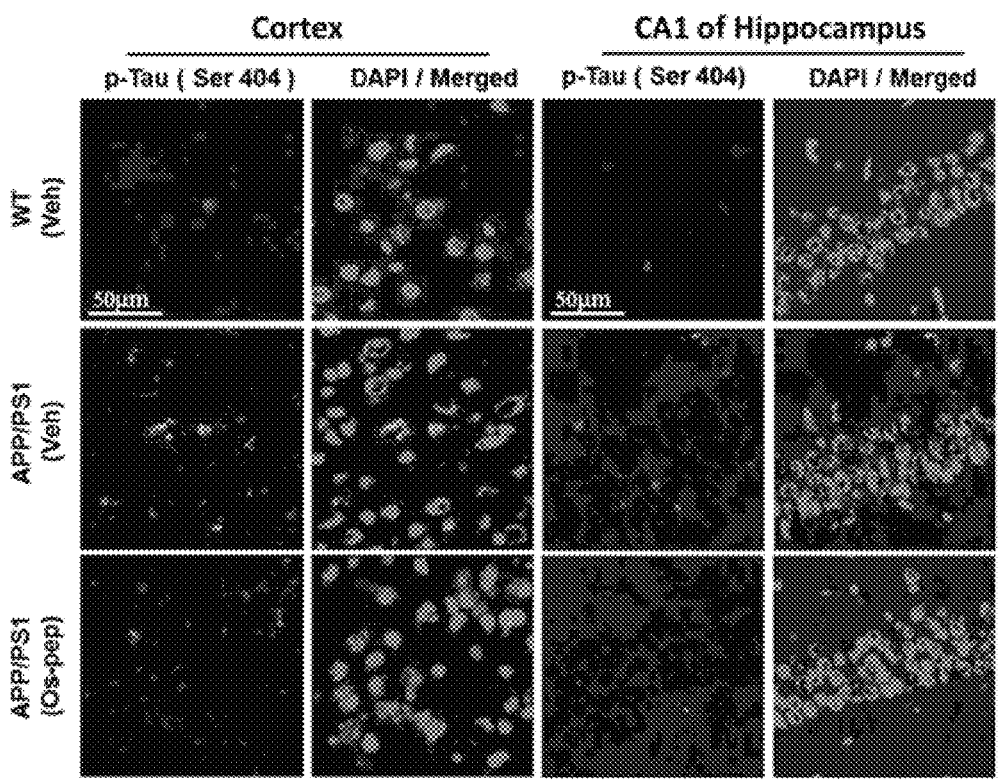
FIGS. 6A and 6B show that the expression of p-Tau (Ser 404) is decreased in the cerebral cortex and hippocampal sites when APP/PS1 mice are treated with osmotin peptide. *** indicates statistically significant increase in expression of p-Tau (Ser 404) in the APP/PS1 model compared to WT (normal control), and, in this case, the p value is less than 0.001. ### means that the expression of p-Tau (Ser 404) is statistically significantly reduced compared to the APP/PS1 model when osmotin peptide is treated, and, in this case, the p value is less than 0.001.
Figure 6B:
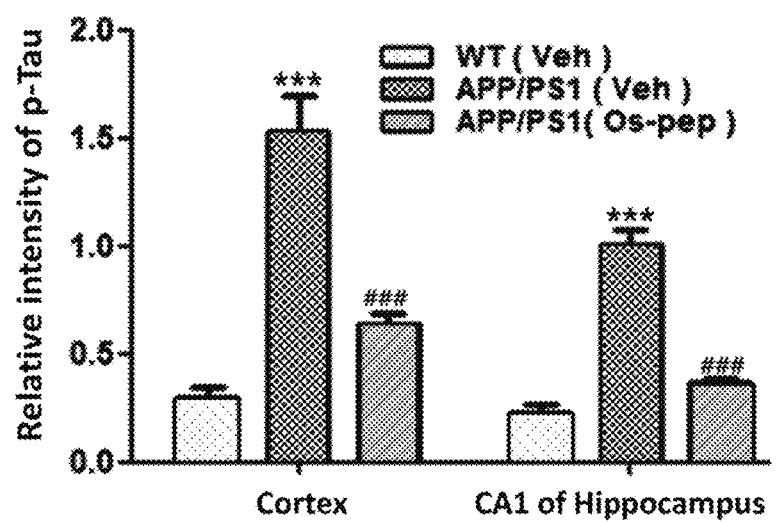
Figure 7:
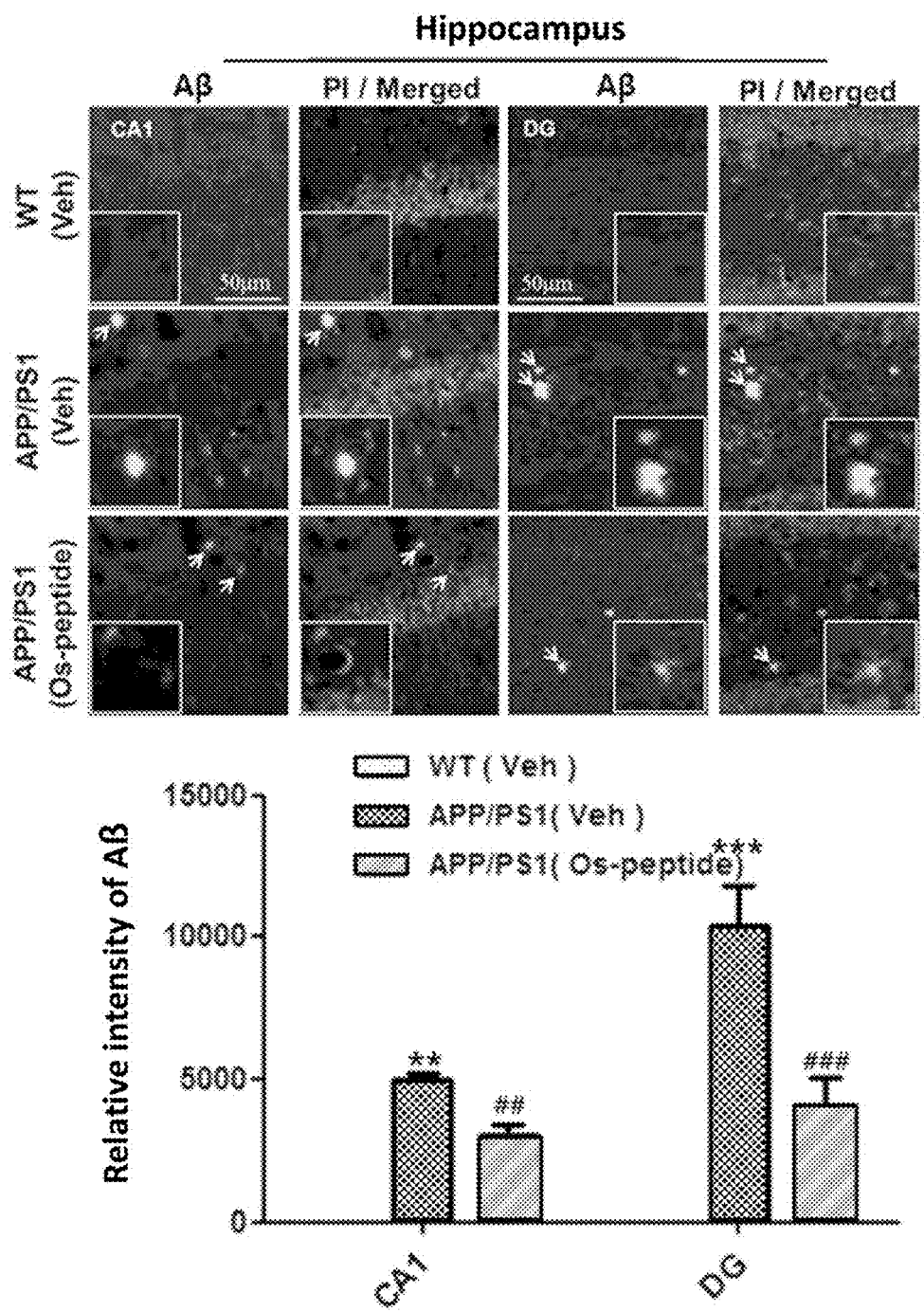
FIG. 7 shows significant reduction in Aβ plaques in CA1 and DG sites of the brain hippocampus due to the osmotin peptide treatment to APP/PS1 mice.  and * indicate the statistical significance increase in the expression of Aβ plaque in the APP/PS1 model compared to WT (normal control), wherein, in the case of , the p value is less than 0.01, and in the case of *, the p value is less than 0.001. ## and ### indicate that the expression of Aβ plaques is statistically significantly reduced compared to the APP/PS1 model when osmotin peptide is treated, wherein, in the case of ##, the p value is less than 0.001, and in the case of ###, the p value is less than 0.001.
Figure 8:
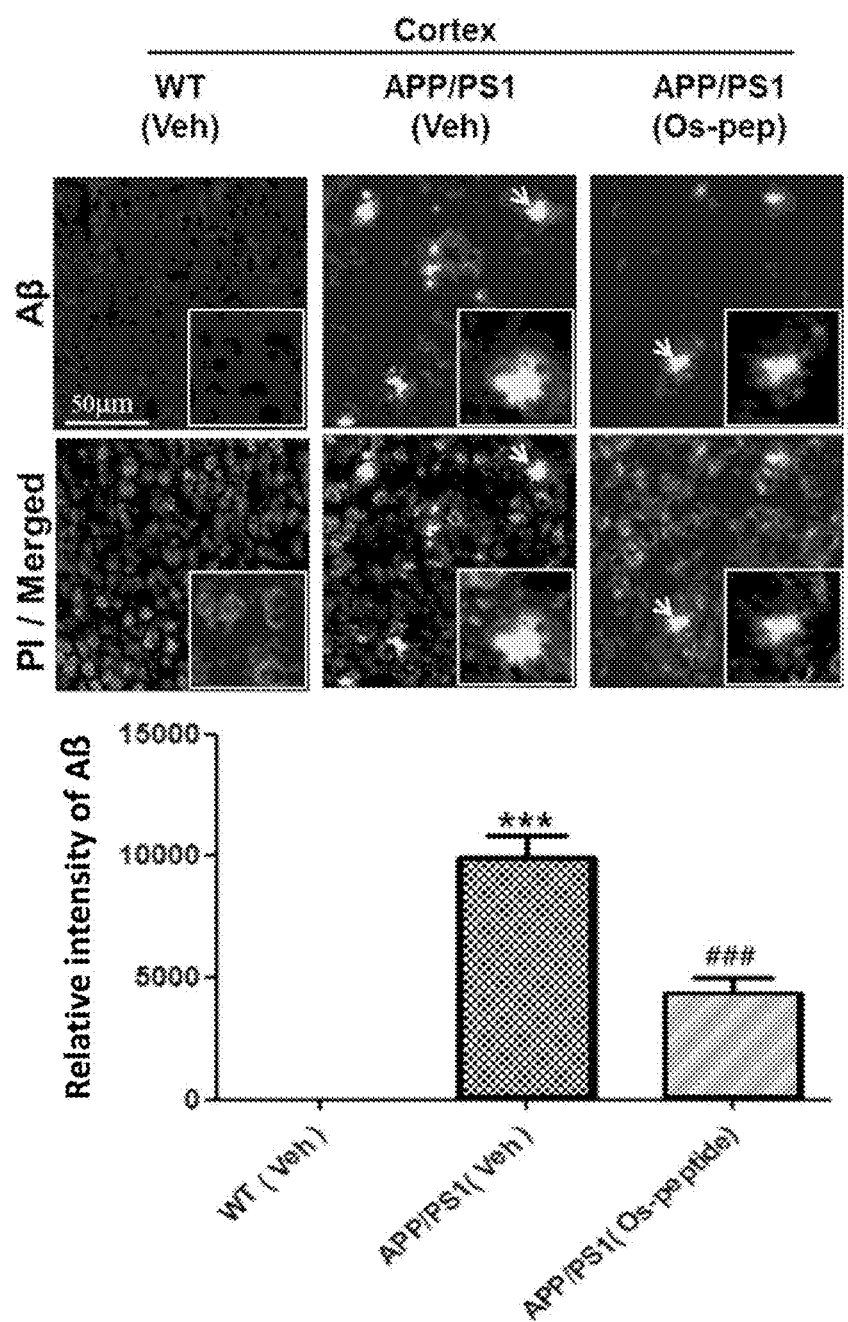
FIG. 8 shows that the Aβ plaque is reduced in the cerebral cortex when APP/PS1 mice are treated with osmotin peptide. * indicates statistically significant increase in the expression of Aβ plaques in the APP/PS1 model compared to WT (normal control), and, in the case of *, the p value is less than 0.001. ### means that the expression of Aβ plaques is statistically significantly reduced compared to the APP/PS1 model when osmotin peptide is treated, and, in the case of ***, the p value is less than 0.001.

As shown in FIG. 3, it was confirmed that after intraperitoneal (IP) injection and tail vein injection (IV) to the mouse, osmotin-peptide according to the present disclosure migrated to the hippocampus of the brain, and after intravenous injection, the osmotin-peptide migrated to cortex and hypothalamus of the brain (FIG. 4).

In addition, as shown in FIGS. 5A, 5B to 8, it was confirmed that Tau-46, p-Tau (Ser 404) and amyloid beta (Aβ) plaques produced in the hippocampus and cerebral cortex of the brain are remarkably reduced by treatment with osmotin peptide treatment.

Example 5. Western Blot Analysis 10 mg of tissue was extracted in 600 μl of PRO-PRO-PREP (Intron Biotech) protein extraction solution at 4° C. according to the manufacturers instructions. Protein concentration was determined by using a Bio-Rad protein assay kit. 20 mg of protein degradation product was separated by SDS-PAGE at 4-12% (v/v). Thereafter, the SDS-PAGE gel was transferred to a membrane and blocked with 5% skim milk.

The resultant protein was treated with primary antibody at 4° C. and incubated overnight, and then reacted with secondary antibody fused with horseradish peroxidase (HRP), and treated with the ECL solution. Primary antibodies used herein were phospho-Tau (Ser 413), phospho-Tau (Ser 404), BACE-1 (Beta-secretase 1), amyloid beta (Aβ) oligomer, APP, BACE-1, Syanpatophysin, SNAP25 (Synaptosomal-Associated Protein 25), PSD95 (postsynaptic density protein 95), AdipoR1 (Adiponectin receptor 1), phospho-AMPK, AMPK (AMP-activated protein kinase), β-actin, phospho-JNK, TNF-α, NF-κB, and phospho-IKKβ.

As a negative control, a normal medium that does not provide APP was used. As a positive control, an APP-supplemented medium was used. As an experimental group, osmotin (0.1 to 20 μM) was used.

Figure 9:
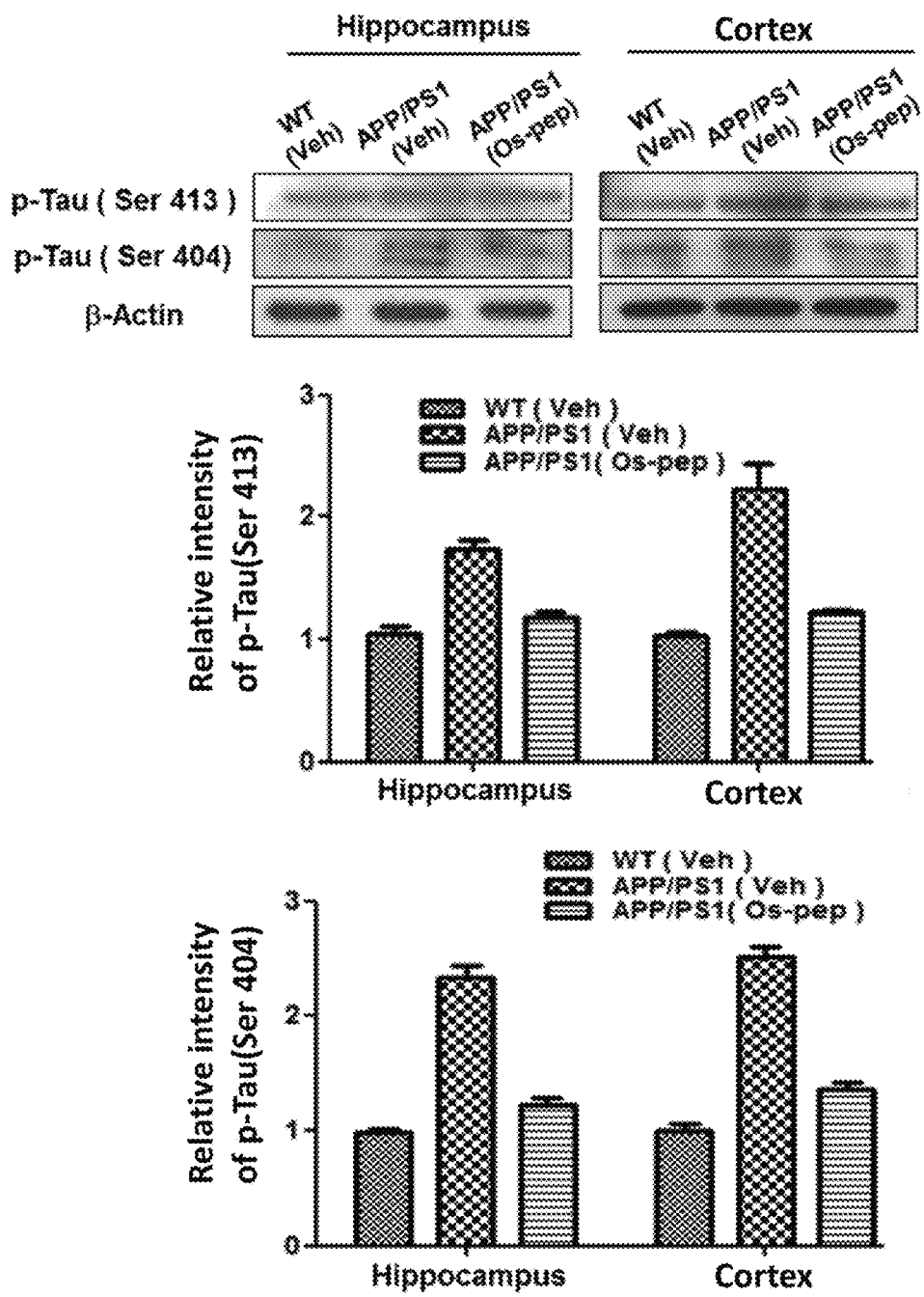
FIG. 9 shows that the p-Tau (Ser 413) and p-Tau (Ser 404) proteins produced in the hippocampus and cerebral cortex of the APP/PS1 mice brain are reduced by treatment with osmotin peptide.
Figure 10:
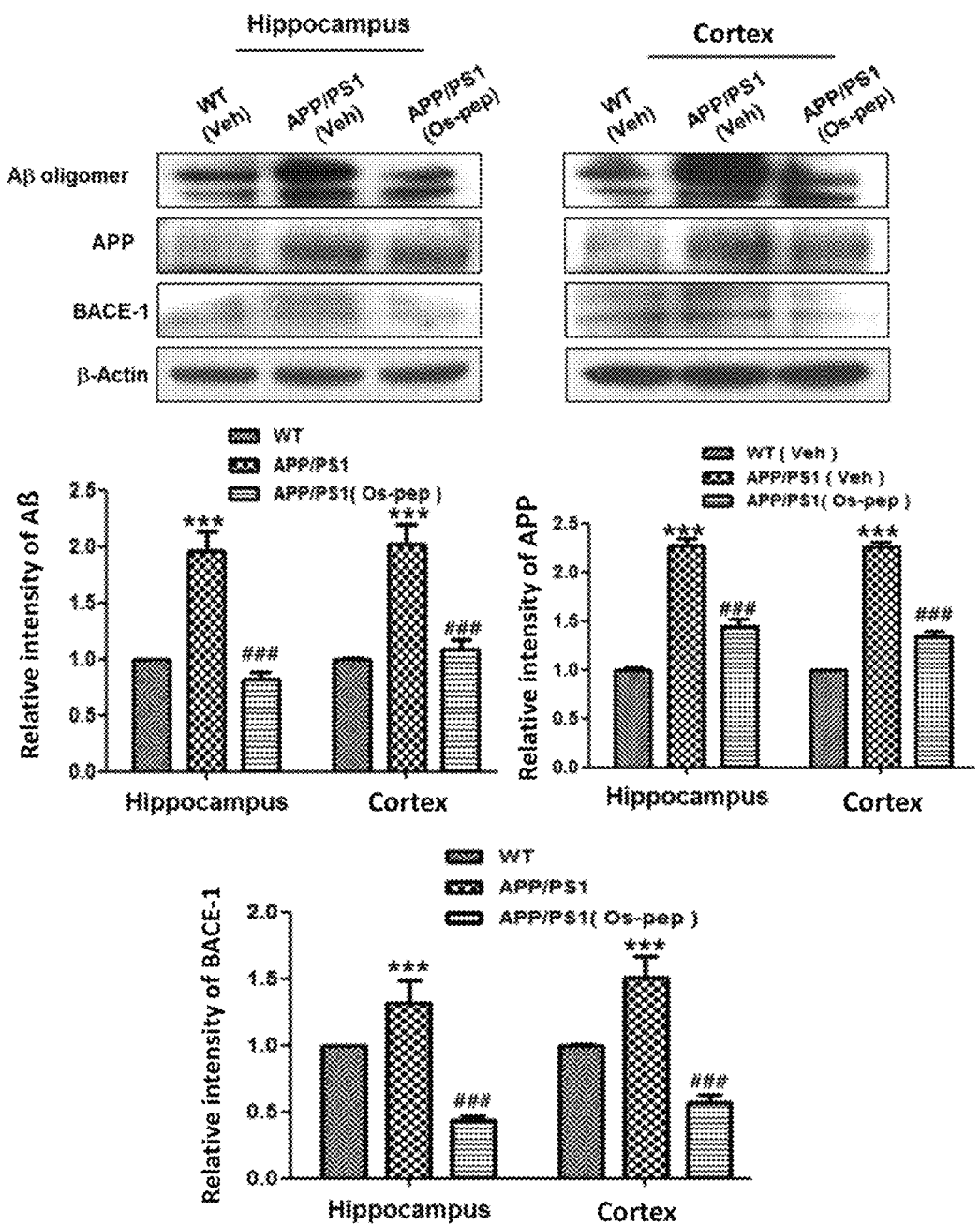
FIG. 10 shows that amyloid-8 oligomer or Aβ oligomer, APP and BACE-1 proteins produced in the hippocampus and cortex of the APP/PS1 mice brain are reduced by treatment with osmotin peptide.
Figure 11:
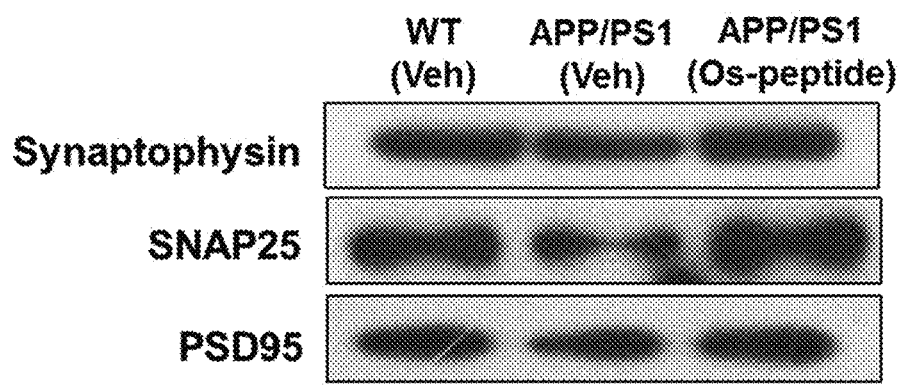
FIG. 11 shows that the expression levels of SNAP25 and PSD95 protein expressed by the enhancement of synaptic function are increased by treating APP/PS1 mice with osmotin peptide.

The results are shown in FIGS. 9 to 11 and it was confirmed that the expression levels of p-Tau (Ser413), p-Tau (Ser404), Aβ oligomer, APP and BACE-1 protein in the hippocampus and cerebral cortex were markedly decreased (FIG. 9 and FIG. 10), and SNAP25 and PSD95 proteins, which enhance synaptic function, were increased in expression (FIG. 11).

Figure 12:
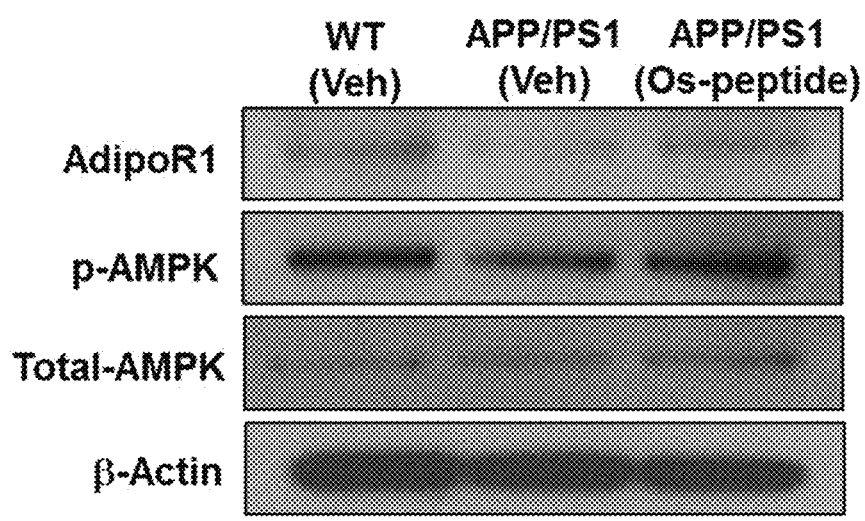
FIG. 12 shows that the expression levels of AdipoR1, pAMPK and total-AMPK are increased by treating APP/PS1 mice with osmotin peptide.
Figure 13:
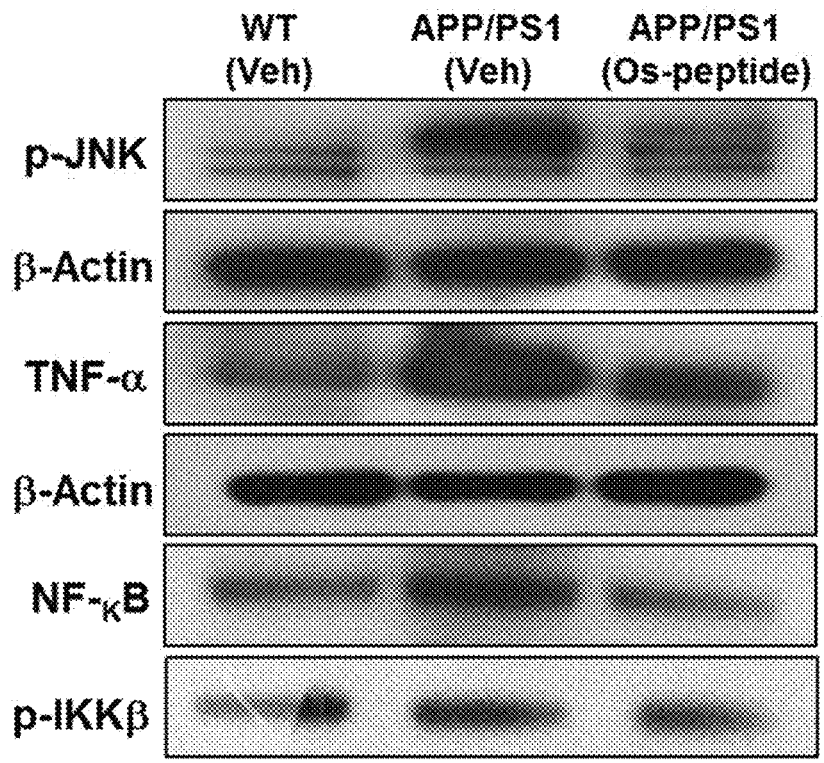
FIG. 13 shows that the expression levels of p-JNK, TNF-α, NF-κB, and pIKKβ proteins are decreased by treating APP/PS1 mice with osmotin peptide.
Figure 14:
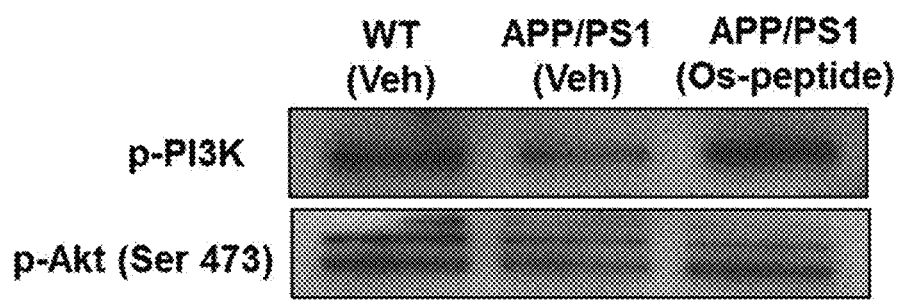
FIG. 14 shows that the expression levels of p-PI3K and pAkt (Ser473) proteins are increased by treating APP/PS1 mice with osmotin peptide.

In addition, due to the treatment with osmotin peptide, the expression levels of AdipoR1, pAMPK and total-AMPK proteins were increased (FIG. 12), the expression levels of pJNK, TNF-α, NF-κB and p-IKKβ proteins were decreased (FIG. 13), and the expression levels of p-PI3K and pAkt (Ser473) were increased (FIG. 14). These results show that osmotin peptide regulates intracellular signaling inside nerve cells.

Example 6. Behavioral Analysis

1) Model Animal and Drug Treatment

To confirm the behavioral analysis according to the treatment with the osmotin peptide, which is an active ingredient, according to the present disclosure, male C57BL/6J wild-type mice and double transgenic B6.Cg-Tg (APPswe, PSENdE9) 85Dbo/Mmjax (APP/PS1) AD-model mice were purchased from Jackson Laboratories (Bar Harbor, Me., USA). The double transgenic mouse expresses, in its brain, a mutant human presenilin 1 protein (PS1-dE9) as well as a chimeric mouse-human amyloid precursor protein (Mo/HuAPP695swe) containing a Swedish mutation, and after the purchase, the mice were fed with unlimited food and water at the animal breeding grounds of a university under a contrast cycle of 12 h/12 h at a temperature of 23° C., in a 10% relative humidity. When the mice reached 10 months of age, they were transferred to the injection and behavior observation room for 1 week for purification. Mouse maintenance and treatment were performed according to the guidelines of the Institutional Animal Care and Use Committees (IACUC) issued by the Department of Applied Life Sciences of the Gyeongsang National University. Mouse experiments described herein were conducted according to the guidelines (approval ID: 125) approved by the IACUC of the Department of Applied Life Sciences of the Gyeongsang National University.

The animals used in Example 6 were grouped as follows.

1) Normal group: wild-type (WT) group (a group not treated with osmotin peptide according to the present disclosure), 2) APP/PS1 transformed group (a group not treated with osmotin peptide according to the present disclosure), 3) APP/PS1 transformed group treated with the osmotin peptide according to the present disclosure as an active ingredient, and 4) WT group treated with osmotin peptide according to the present disclosure as an active ingredient.

The osmotin peptide according to the present disclosure was dissolved in bi-deionized distilled water, and finally prepared using physiological saline and administered. The osmotin peptide according to the present disclosure was administered intraperitoneally (i.p.) to APP/PS1 and wild-type (WT) mice at a dose of 5 mg/kg/day for 45 days according to body weight. WT mice and APP/PS1 transformed mice were treated with the same volume of physiological saline, and after behavioral analysis, the animals were sacrificed for further biochemical and immunohistochemical analysis.

The behavioral study of Example 6 was performed with 13 mice per group by using the Morris water maze (MWM) test and the Y-maze test.

1) MWM Test

A MWM test system included a round water tank with a diameter of 100 cm and a height of 40 cm, which contains water with the depth of 15.5 cm (water temperature 23±1° C.) opaque with white ink added. A transparent evacuation platform (10 cm in diameter, 20 cm in height) was hidden 1 cm below the water surface and placed in the center of one of the quadrants. Each mouse was trained daily for five consecutive days using three quadrants of rotational starting and one platform hidden in one quadrant. The latency to escape from the water maze (time to find the hidden escape platform) was calculated for each trial. Twenty-four hours after the fifth day, a probe experiment was performed for memory enhancement evaluation. The probe experiment was performed as follows: the platform was removed, and each mouse was allowed to freely swim for 60 seconds, and the time the mouse spent in the target quadrant and the number of the location of the platform (where the platform was located during hidden platform training) the mouse passed. The time spent in the target quadrant was used as a reference indicating the degree of memory enhancement. All data were recorded by using video-tracking software (SMART, Panlab Harward Apparatus, Bioscience Company, Holliston, Mass., USA).

Figure 15A:
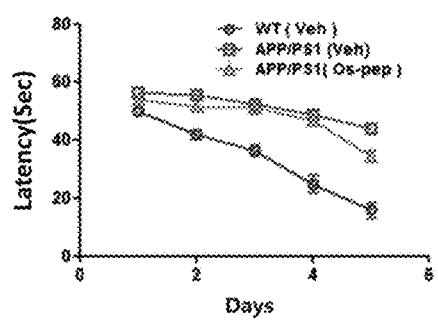
FIGS. 15A to 15D show results of several tests for confirming behavioral change after 45 days of intraperitoneal (IP) injection of osmotin peptide to Alzheimer's mouse: latency of the Morris water maze experiment; the number of passes through the platform intersection in the probe test of the Morris Water maze experiment; time to stay in target quadrant in the Morris water maze experiment; and spontaneous alteration (%) of the Y-maze test.
Figure 15B:
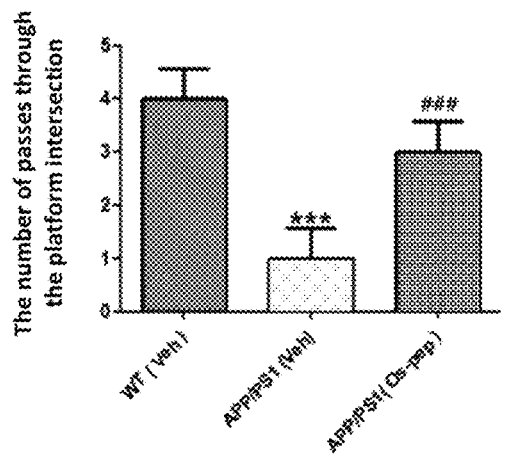
Figure 15C:
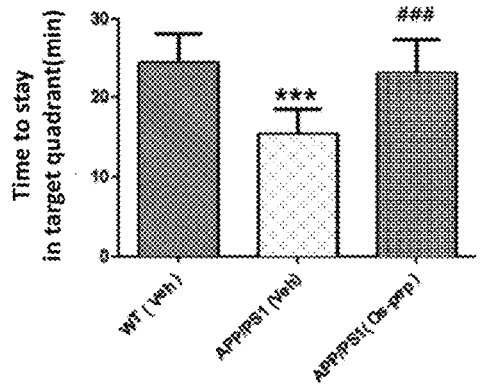

As shown in FIGS. 15A to 15D, in the case of the normal mice, the latency, which is the delay time for escaping from the water maze (the time for finding the hidden escape platform), was significantly reduced by training for 5 days, down to no more than 20 seconds. However, the latency of the APP/PS1 model mouse is about 45 seconds, and the latency of the APP/PS1 model mouse treated with the adiponectin receptor-activated osmotin peptide according to the present disclosure was reduced down to about 33 seconds (FIG. 15A). In addition, even results of the probe test showed that, in the case of the APP/PS1 model mouse, the number of staying at the place where the platform had been located was tended to be significantly smaller than that of the normal mouse. When the APP/PS1 model mouse was treated with osmotin peptide, the number of staying at the place where the platform had been located was increased, compared with the APP/PS1 model mice (FIG. 15B). In the case of the APP/PS1 model mouse, the time spent in the target quadrant decreased significantly compared to that of the normal mouse. However, in the case of the mouse treated with the osmotin peptide used as an active ingredient according to the present disclosure, the active ingredient of the present disclosure, the time spent in the target quadrant increased to almost the same level as that of the normal mouse (FIG. 15C).

2) Y-Maze Test

The Y-maze was made of black painted wood, and each arm of the Y-maze had a length of 50 cm, a height of 20 cm, and a bottom and a top each having a width of 10 cm. Each mouse was placed in the center of a maze device, and allowed to move freely in the maze during three 8-minute sessions. The series of arm entries into the arms of the Y-maze were visually observed. Spontaneous alteration was defined as the case in which the mice sequentially enter three different branches in overlapping triplet sets.

An alteration behavior ratio (%) was calculated as [overlapping triplet sets (the case in which the mice sequentially enter three different branches)/total entries−2]×100. A high spontaneous alteration ratio was considered to be an improvement in memory function.

Figure 15D:
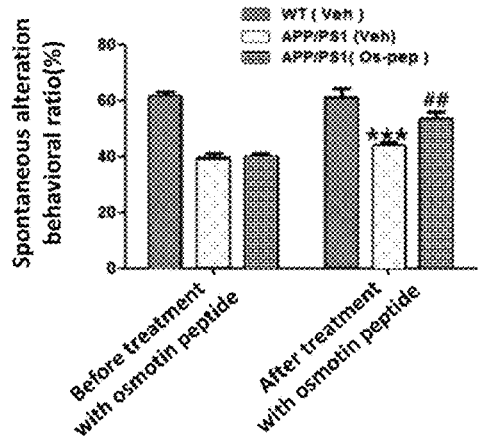

As a result of the Y-maze test, it was confirmed that as shown in FIG. 15D, the spontaneous alteration was reduced in the APP/PS1 model mouse as compared with the normal mouse, and due to the treatment with osmotin peptide, the spontaneous alteration was restored.

From the behavioral analysis of APP model mice, it was considered that the treatment with osmotin peptide according to the present disclosure leads to an improvement in cognition or memory.

Example 7. In Vitro Electrophysiological Analysis [Long-Term Potentiation (LTP)]

In Example 7, for in vitro electrophysiology analysis, primary hippocampal neurons isolated from E19 Sprague- Dawley rats were cultured to a density of 150 cells/mm². Miniature excitatory postsynaptic currents (mEPSCs) mediated by the AMPA receptor (AMPAR) were recorded by using conventional whole-cell techniques. When filled with an internal solution, an electrode resistance varied from 3 to 5 MΩ.

In Example 7, the current was measured by using an Axopatch 200A patch-clamp amplifier (Molecular Devices, Sunnyvale, Calif.).

Membrane voltage and current voltage, command, and digitization were controlled using a Digidata 1322A connected to Clampex 9.2 (Molecular Devices, Sunnyvale, Calif.) of the pClamp software package on an IBM-compatible computer, data was analyzed by using a Clampfit (Molecular Devices, Sunnyvale, Calif.) and Prism 4.0 (GraphPad, San Diego, Calif.), and the current was low-pass filtered at 2 kHz by using an amplifier's four-pole Bessel filter.

Figure 16:
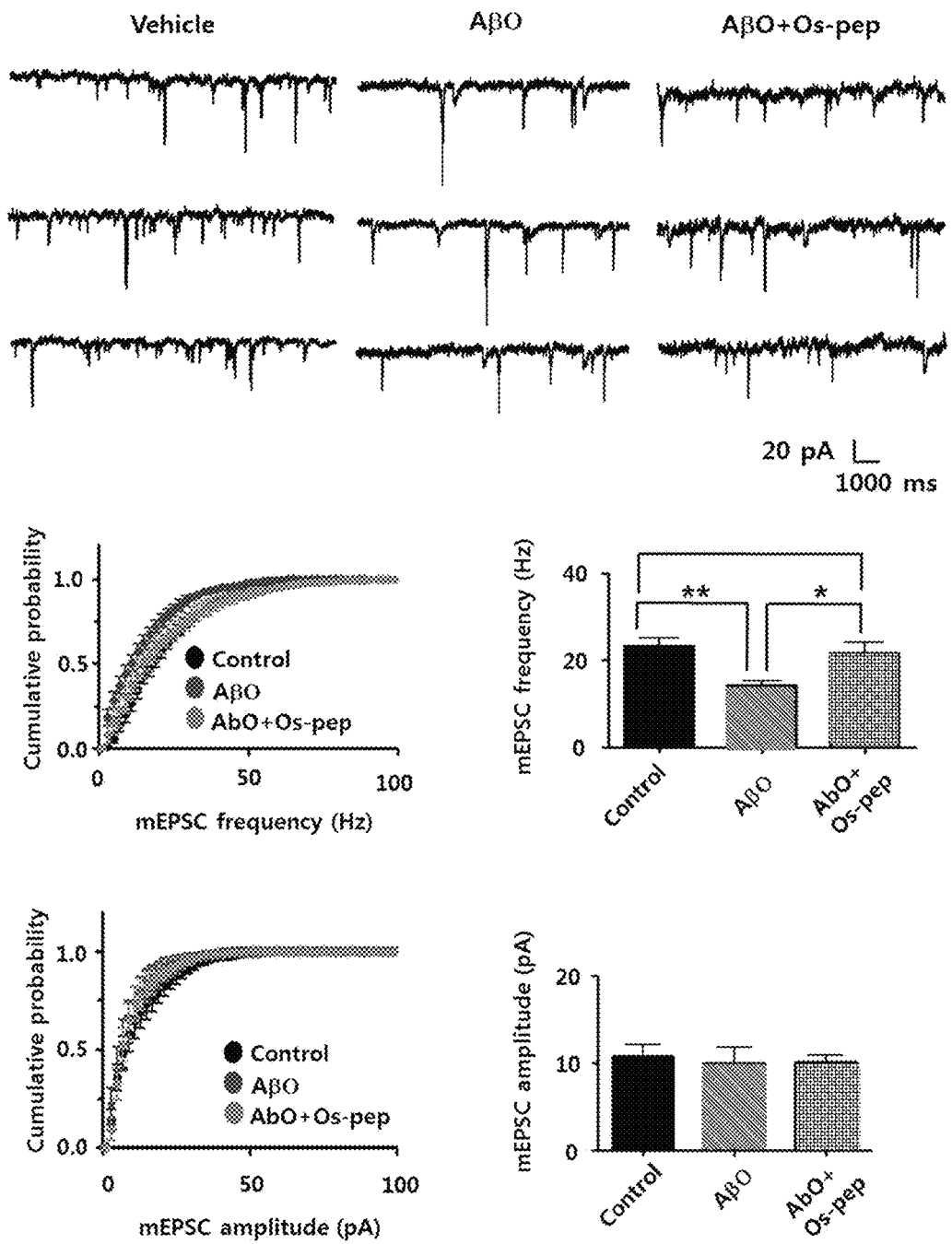
FIG. 16 shows values of long-term potentiation (LTP) of hippocampal neurons of model mice cultured, wherein LTP are electrophysiologically measured, confirming that the mEPSC frequency (Hz) is increased in the group treated with the osmotin peptide according to the present disclosure.
Figure 17A:
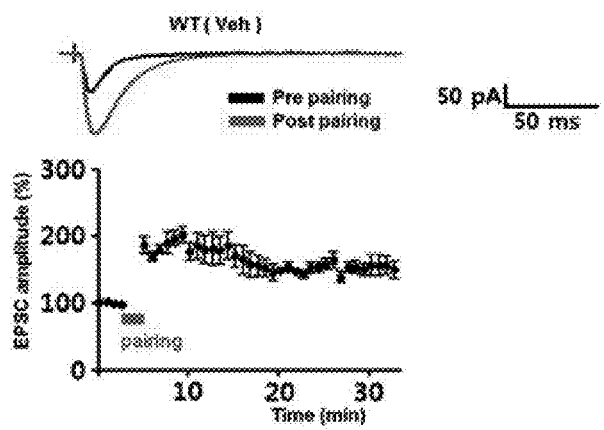
FIGS. 17A to 17D show values of in vivo LTP, confirming the degree of EPSC enhancement in the normal group, the APP/PS1 mouse model group, and the APP/PS1 mouse model group treated with osmotin peptide.
Figure 17B:
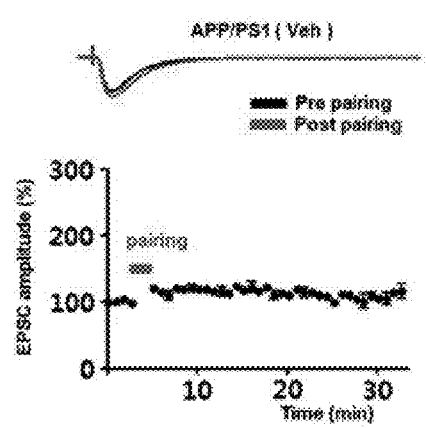
Figure 17C:
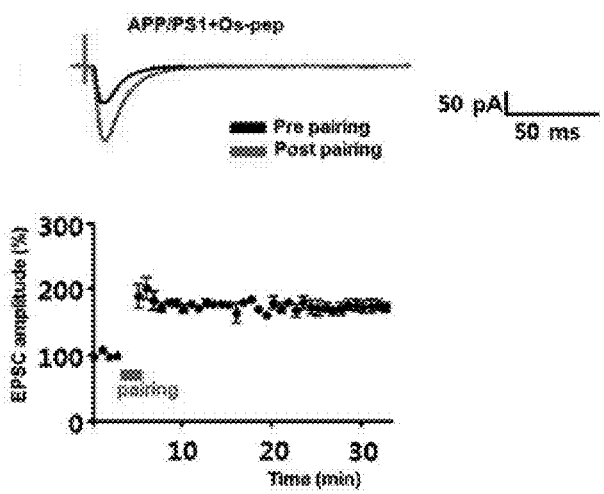
Figure 17D:
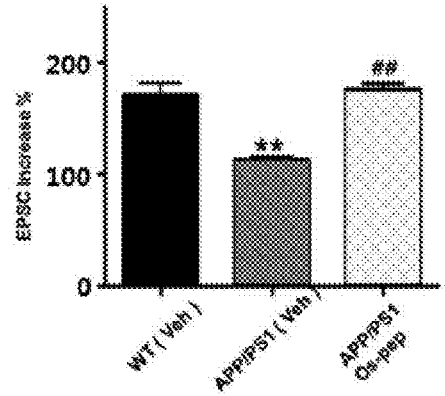

AMPAR-mEPSCs were electrophysiologically separated by adding 1 mM tetrodotoxin and maintaining a Cl⁻ equilibrium potential of −70 mV in the internal and external solution configurations according to the present disclosure. An intracellular recording solution (patch electrode) included 125 mM Cs methanesulfonate, 8 mM NaCl, 10 mM HEPES, 0.5 mM EGTA, 4 mM Mg-ATP, 0.3 mM Na-GTP and 5 mM QX-315Cl (pH 7.25, titration with CsOH, 285 mosmol$^{-1}$). An extracellular recording solution included 134 mM NaCl, 5.4 mM KCl, 2.5 mM $CaCl_2$, 1.2 mM $MgCl_2$, 10 mM D-glucose, and 10 mM HEPES (pH 7.4, titrated with NaOH). For each cell, data was filtered at 2 kHz and analyzed using template-based miniature synaptic current detection algorithms implemented in Clampfit 9.0 software (Molecular Devices, Union City, Calif.). Each estimated mEPSC detected by software was accepted or rejected based on whether its general form is visually the same as expected for synapse phenomena. 300 consecutive mEPSCs that satisfy rise time criteria, were analyzed in each cell. The AMPAR-mediated EPSC amplitude was measured at the peak of the current at −70 mV (FIG. 16).

Cumulative probability curves for mEPSCs were calculated with Clampfit 9.0 software and Prism 4.0 (GraphPad, San Diego, Calif.). As shown in FIG. 16, the frequency (Hz) of the Aβ group in Example 7 was significantly reduced compared with the normal group (vehicle), and the reduced frequency (Hz) was enhanced by the treatment with the osmotin peptide, and the enhanced effect was statistically significant. The present inventors used Student's t-test to compare the two groups. Differences were considered statistically significant at $p<0.05$.

Example 8. In Vivo Electrophysiology and LTP Analysis

Hippocampal slices (each having a thickness of 400 μM) were prepared from adult mice to investigate the CA1 circuit from the cross-sectional schaffer collateral (SC) input in the hippocampal slices. Briefly, after anesthetizing the mouse with isoflurane, the brain was quickly cooled by transcardiac perfusion with ice cold sucrose-artificial cerebrospinal fluid (CSF). The brain was removed and stored in an ice-cold sucrose-artificial CSF. Coronal sections were incubated in artificial CSF at 35° C. for 30 minutes and cultured in artificial CSF for 1-4 hours at room temperature (23-25° C.) before being transferred to a recording chamber. The standard artificial CSF contained 95% $O_2$ and 5% $CO_2$-saturated 119 mM NaCl, 2.5 mM KCl, 2.5 mM $CaCl_2$, 1.3 mM $MgSO_4$, 1.0 mM $NaH_2PO_4$, 26.2 mM $NaH_2CO_3$, 11 mM glucose, 1 mM Na pyruvic acid, and 0.4 mM Na ascorbic acid, and the ucrose-artificial CSF included 95% $O_2$ and 5% $CO_2$-saturated 198 mM sucrose, 2.5 mM KCl, 1 mM $NaH_2PO_4$, 26.2 mM $NaHCO_3$, 11 mM glucose, 1 mM Na pyruvic acid, and 0.4 mM Na ascorbic acid.

LTP experiments were carried out at a temperature of 27° C. to 29° C. For electrophysiological experiments, electrodes with 3-6 MΩ pipette resistance were used, and whole-cell recordings were obtained from neurons under visual guidance by using infrared (IR)-differential interference contrast (DIC) optical guideline. CA3 and DG regions were cleaved just before the start of LTP experiments to isolate CA1 lesions. Stimulation was applied to the shaperside branch (SC) pathway using a concentric bipolar electrode located at 100-200 mM from the soma of the recorded cells. The whole cell recording solution was as follows: 135 mM Cs methanesulfonate, 8 mM NaCl, 10 mM HEPES, 0.5 mM EGTA, 4 mM Mg-ATP, 0.3 mM Na-GTP and 5 mM QX-315Cl (pH 7.25, titrated with CsOH, 285 MOsm). Cells were maintained at −70 mV during recording, unless indicated otherwise. The recordings were made using a multiclamp 700B (molecular devices, sunnyvale, Calif.) digitized at 10 kHz and filtered at 2 kHz. Input resistance and series resistance were continuously observed during recording. The test stimulus for all EPSC experiments was set at 0.1 Hz, and the duration of 0.2 ms and its intensity (100-900 μA) were adjusted to derive EPSC amplitudes from 50 to 100 pA with a maintenance potential of −70 mV. In the LTP experiment, baseline EPSCs were measured for 3 minutes before application of pairing stimuli (2 Hz, 2 min stimulation and post-synaptic depolarization to 0 mV). After the pairing stimuli (2 Hz, 2 min stimulation and post-synaptic depolarization to 0 mV, followed by depolarization), EPSCs were collected every 10 min for 30 minutes.

As shown in FIGS. 17A to 17D, in the normal group, synaptic transmission was enhanced in the long term by the input of the pairing stimulus, but in the APP/PS1 model group, the EPSC enhancement was statistically significantly decreased. However, the APP/PS1 model group treated with adiponectin receptor-stimulated osmotin peptide showed almost the same level of EPSC enhancement compared to the normal group.

The invention claimed is:

1. A method of treating Alzheimer's disease, the method comprising administering to a subject having the Alzheimer's disease, a composition comprising an osmotin peptide consisting of SEQ ID NO: 1.

2. The method of claim 1, wherein the osmotin peptide is contained in an amount of 0.1 to 100% by weight based on the total weight of the composition.

3. The method of claim 1, wherein the composition is a health functional food in any one formulation selected from the group consisting of a beverage, a pill, a tablet, a capsule, and powder.

4. The method of claim 1, wherein the composition is a pharmaceutical composition.

5. The method of claim 4, further comprising, in addition to the active ingredient, at least one carrier selected from saline, sterilized water, Ringer's solution, buffered saline, dextrose solution, maltodextrin solution, glycerol, ethanol, lactose, dextrose, sucrose, sorbitol, mannitol, starch, acacia rubber, calcium phosphate, alginate, gelatin, calcium silicate, microcrystalline cellulose, polyvinylpyrrolidone, cellulose, syrup, methylcellulose, methylhydroxybenzoate, propylhydroxybenzoate, talc, magnesium stearate, and minerals oil, each of which is pharmaceutically acceptable.

6. The method of claim 4, further comprising, in addition to the active ingredient, at least one supplement selected from antioxidants, buffers, bacteriostats, diluents, surfactants, binders, lubricants, wetting agents, sweeteners, flavors, emulsifiers, suspending agents, and preservatives, each of which is pharmaceutically acceptable.

7. The method of claim 1, wherein the subject is a human.

8. The method of claim 1, wherein the subject is an animal.

9. The method of claim 1, further comprising, in addition to the active ingredient, bacteriostats and at least one of polyvinylpyrrolidone, methylhydroxybenzoate, and propylhydroxybenzoate.

* * * * *

SEQUENCE LISTING

<160> NUMBER OF SEQ ID NOS: 1

<210> SEQ ID NO 1
<211> LENGTH: 9
<212> TYPE: PRT
<213> ORGANISM: Artificial Sequence
<220> FEATURE:
<223> OTHER INFORMATION: synthetic peptide

```
<400> SEQUENCE: 1

Cys Thr Gln Gly Pro Cys Gly Pro Thr
1               5
```